United States Patent [19]

Umemoto et al.

[11] Patent Number: 5,030,719

[45] Date of Patent: Jul. 9, 1991

[54] CYTOTOXIC ANTIBODY CONJUGATES AND A PROCESS FOR PREPARATION THEREOF

[75] Inventors: Naoji Umemoto; Yoshinori Kato, both of Hino; Takeshi Hara, Hachioji, all of Japan

[73] Assignee: Teijin Limited, Osaka, Japan

[21] Appl. No.: 196,188

[22] PCT Filed: Aug. 24, 1987

[86] PCT No.: PCT/JP87/00625
§ 371 Date: Apr. 27, 1988
§ 102(e) Date: Apr. 27, 1988

[87] PCT Pub. No.: WO88/01513
PCT Pub. Date: Mar. 10, 1988

[30] Foreign Application Priority Data

Aug. 28, 1986 [JP] Japan .................................. 61-200142
Nov. 19, 1986 [JP] Japan .................................. 61-273953
Jul. 8, 1987 [JP] Japan .................................. 62-168559

[51] Int. Cl.$^5$ ..................... C07K 17/06; A61K 39/44
[52] U.S. Cl. .................................... 530/391; 530/389; 530/402; 530/409; 530/410; 424/85.91
[58] Field of Search ..................... 424/85.91; 530/391, 530/402, 389, 409, 410

[56] References Cited

U.S. PATENT DOCUMENTS

4,203,898  5/1980  Cullinan et al. ..................... 540/478
4,376,765  3/1983  Trouet et al. ......................... 514/18
4,671,958  6/1987  Rodwell et al. ................. 424/85.91

FOREIGN PATENT DOCUMENTS

0122132  10/1984  European Pat. Off. ......... 424/85.91
7900515  8/1979  PCT Int'l Appl.

OTHER PUBLICATIONS

Aboud-Pirak et al. (1989) Biochem. Pharmacol. 38(4)-641-648.
Baurain et al., *Drugs Exptl. Clin. Res. IX*, 4:303-311 (1983).
Kulkarni et al., (1981), Cancer Res. 41:2700-2706.
Trouet et al., (1982), Proc. Natl. Acas. Sci. 79:626-629.
Umemoto et al., (1989) Cancer Immunol. Immunother. 28:9-16.
Umemoto et al., (1989) Int. J. Cancer 43:677-684.

*Primary Examiner*—John Doll
*Assistant Examiner*—Kay Kim
*Attorney, Agent, or Firm*—Sughrue, Mion, Zinn Macpeak & Seas

[57] ABSTRACT

Cytotoxic antibody conjugates in which a folic acid-antagonistic folic acid analogue is bound to an antibody or its fragment through an oligopeptide. The conjugates can be used as a chemotherapeutic agent against malignant tumors.

7 Claims, No Drawings

CYTOTOXIC ANTIBODY CONJUGATES AND A PROCESS FOR PREPARATION THEREOF

FIELD OF THE ART

The present invention relates to cytotoxic antibody conjugates.

Particularly, the present invention relates to cytotoxic antibody conjugates in which a folic acid-antagonistic folic acid analogue is conjugated with an antibody selectively binding to a specific antigen in the cells to be killed or its fragment including the antigen-binding site through an oligopeptide, and a process for preparation thereof.

BACKGROUND OF THE ART

A folic acid-antagonistic folic acid analogue means a substance which has a chemical structure similar to folic acid, but inhibits partially or totally the actions of folic acid or its derivatives. A variety of such substances have been synthesized and some of them have been applied to the chemotherapy for cancers such as leukemia or malignant tumors.

It has been known that a cytotoxic conjugate of a folic acid-antagonistic folic acid analogue with an antibody is formed by linking methotrexate with the antibody using a water-soluble carbodiimide as a condensation agent or using an active ester of methotrexate (see P.N. Kulkarni et al.: Cancer Research 41, 2700–2706, 1981). Further, M.C. Garnet disclosed a method of conjugating methotrexate with an antibody via serum albumin as an intermediary (Int. J. Cancer, 31, 661–670, 1983). Neither, however, the process for conjugation of a folic acid-antagonistic folic acid analogue with an antibody or its fragment via an oligopeptide nor such a cytotoxic antibody conjugate have been known. Conventional conjugates resulting from direct conjugation of methotrexate with an antibody is unsatisfactory in potency and selectivity of cytotoxicity and antitumor activity, while oligopeptide-mediated conjugates seem to meet the expectation of resolving these problems.

DISCLOSURE OF THE INVENTION

The present inventors have made intense study on the development of procedures for conjugating a folic acid-antagonistic folic acid analogue with an antibody or its fragment via an oligopeptide and of useful cytotoxic antibody conjugates through the processes. The intermediate obtained by linking a folic acid-antagonistic folic acid analogue to an oligopeptide at the N-terminal has carboxyl groups on the folic acid analogue as well as on the C-terminal of the oligopeptide. Therefore, it cannot be bonded to an antibody or its fragment selectively only through the latter carboxyl. The development of a new type of reaction of the intermediate with an antibody or its fragment is required including the derivation of a suitably reactive compound from the intermediate.

The present inventors have reached this invention by finding that a halogenated (especially iodinated or brominated) acetyl hydrazide is high reactive with an antibody or its fragment and the folic acid-antagonistic folic acid analogue can be led to a halogenated acetyl hydrazide derivative through the oligopeptide moiety.

Namely, the present invention relates to cytotoxic antibody conjugates in which a folic acid-antagonistic folic acid analogue is bonded through an oligopeptide and preferably relates to cytotoxic antibody conjugates with excellent cytotoxicity and antitumor properties having a general formula [I]

$$(R'-CO-NH-Y-CO-NHNHCOCH_2-NH)_n-Ab \quad [I]$$

where R' represents, together with CO, the residual group of folic acid-antagonistic folic acid analogue, —NH—Y—CO— represents the residual group of an oligopeptide containing L-leucyl-L-alanyl-L-leucine, Ab represents an antibody or its fragment, the N-atom adjacent to Ab is the nitrogen atom originating from the antibody or its fragment, and n is an integer of from 1 to 30.

The present invention also relates to a general process for preparation of cytotoxic antibody conjugates including the conjugates stated above, in other words, a process for preparation of cytotoxic antibody conjugates of general formula [II]

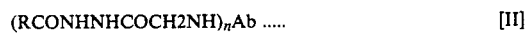

$$(RCONHNHCOCH_2NH)_n Ab \quad [II]$$

where R represents, together with CO, a monovalent organic group originating from the cytotoxic substance, the N-atom linking with Ab originates from the antibody or its fragment, and n is an integer of from 1 to 30, characterized by reaction of an ahtibody or its fragment with a halogenated acetyl hydrazide derivative of a cytotoxic substance having a general formula [III]

$$RCONHNHCOCH_2X \quad [III]$$

where the definition of R is the same as in formula [II], and X represents a halogen.

When the RCO in general formulas [II] and [III] is represented by the following general formula [IV], the resultant cytotoxic antibody conjugate corresponds to formula [I].

$$R'-CO-NH-Y-CO- \quad [IV]$$

where R' represents, together with the adjacent CO, the residual group of a folic acid-antagonistic folic acid analogue, and —NH—Y—CO— represents the residual group of an oligopeptide, preferably the residual group of an oligopeptide containing L-leucyl-L-alanyl-L-leucine.

THE BEST EMBODIMENT OF THE INVENTION

In the present invention, the antibody means an immunoglobulin which can selectively combine with a specific antigen born by the cells to be killed (called target cells hereinafter). Such an antibody is obtained from antiserum separated from an animal such as monkey, horse, cattle, goat, sheep, rabbit and chicken which has been immunized with target cells such as tumor cells or specific lymphocytes, by a known fractionation method such as ethanol fractionation, ammonium sulfate fractionation, ion-exchange or size exclusion column chromatography, protein A-Sepharose column chromatography. Further, the antibody which is used in the present invention is also obtained from the cell culture mixture of transformed cells obtained by virus-transformation of lymphocytes collected from an animal immunized with the target cells or of specific antibody-producing fused cells (hybridoma) between the lymphocytes and myeloma cells or from the serum or peritoneal fluid, after inoculation of these transformed or fused cells in an animal. As an antigen for immunization in the preparation of antiserum or antibody-producing lymphocytes, are also used antigen substances extracted from the target cells or artificially synthesized target cell antigen as well as the target cells. Further, in the preparation of the antibody, the human lymphocytes which, when necessary, have been sensitized with an antigen by treating with an antigen substance can be also used as antibody-producing lymphocytes for cell transformation or fusion. Five classes of antibodies, IgG, IgA, IgM, IgD and IgE have been known as antibodies and any of them is used in the present invention.

In the present invention, the antibody can be used as it is, and further, its fragment also can be employed, as long as it includes the part which combines with the antigen, for example, Fab.

In the present invention, the antibody can also include, when necessary, chemically modified, e.g. acylated products.

The cytotoxic antibody conjugates according to the present invention is generally obtained by reaction of an antibody or its fragment with a halogenated acetyl hydrazide derivative of a cytotoxic substance of general formula (III),

RCONHNHCOCH2X ..... (III)

wherein R represents, together with the adjacent CO, a monovalent organic group originating from cytotoxic substance, and X represents halogen.

In the general formula (III), R represents, together with the adjacent CO group, a monovalent organic group coming from the cytotoxic substance, and a wide range of substances are used as cytotoxic substance, as long as they originally have carboxyl groups or are derivatives bearing carboxyl groups. As suitable cytotoxic substances, for example, the following substances can be used:

Nitrosourea derivative

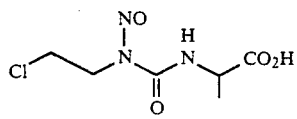

Chlorambucil

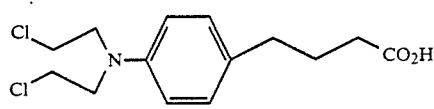

Mitomycin C derivatives

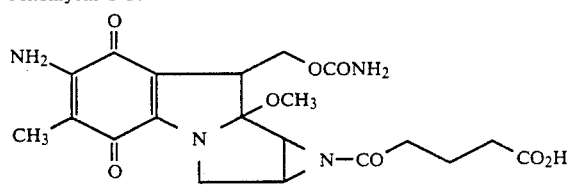

5-Fluoro-2'-deoxyuridine derivative

Desacetylvinblastine derivative

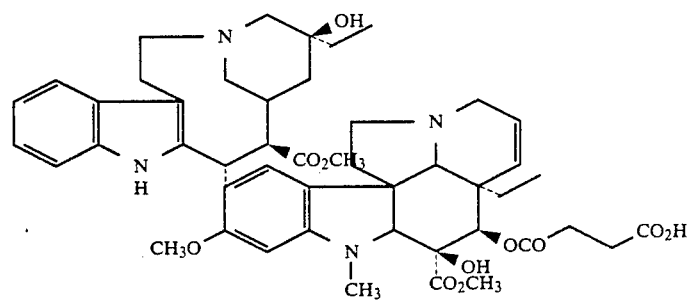

The cytotoxic substances preferably useful in the present invention are folic acid-antagonistic folic acid analogues. The folic acid-antagonistic folic acid analogue means a substance which antagonistically inhibits the actions of folic acid in cells and has a carboxyl-bearing chemical structure similar to the structure of folic acid described below.

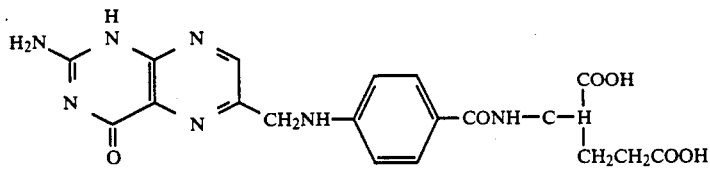

The examples of such substances are methotrexate, aminopterin and 10-ethyl-10-daza-aminopterin.

In the general formula (I), R' represents, along with the adjacent CO group, the residual group of the folic acid-antagonistic folic acid analogue. In other words, it is a monovalent organic group derived from the folic acid-antagonistic folic acid analogue by removing a carboxyl group and the examples of such organic groups are as follows:

(1) methotrexate residues

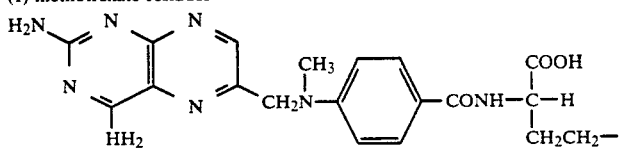

and

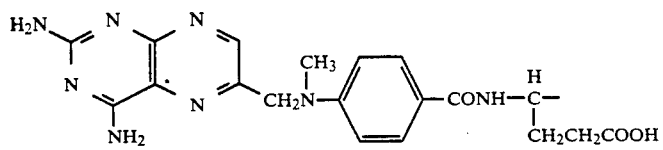

(2) aminopterin residues

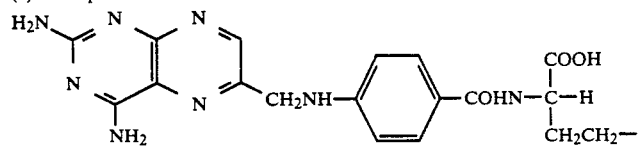

and

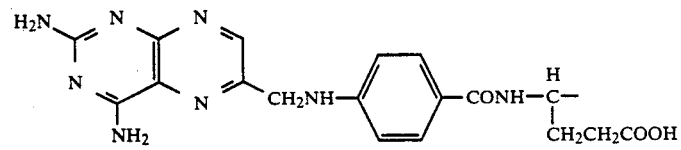

(3) 10-ethyl-10-deaza-aminopterin residues

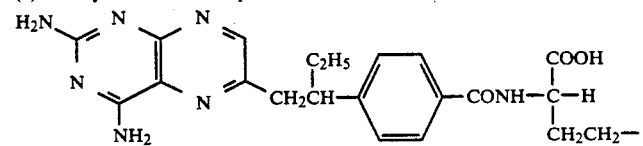

and

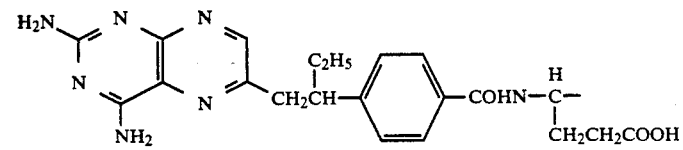

The oligopeptide to be used in the present invention is not limited especially. The number of amino acids is usually 3 to 6 in the oligopeptide. The suitable oligopeptides are, e.g., L-leucyl-L-alanyl-L-leucine, L-leucyl-L-alanyl-L-leucyl-L-alanine, L-alanyl-L-leucyl-L-alanyl-L-leucine, glycyl-glycyl-glycine, glycyl-L-phenylalanyl-L-leucyl-glycine, or glycyl-L-phenylalanyl-L-phenylanlanyl-L-leucine.

In the general formula (III), X is a halogen atom, preferably iodine, bromine or chlorine atom, much preferably iodine or bromine atom.

Further, in the present invention, the oligopeptide containing L-leucyl-L-alanyl-L-leucine sequence is not especially limited, as long as the cleavage of the sequence of L-leucyl-L-alanyl-L-leucine is not inhibited in cells. When the oligopeptide has amino acids other than L-leucine and L-alanine as structural units, however, these amino acids have desirably no functional group of high reactivity. Particularly preferable oligopeptides containing L-leucyl-L-alanyl-L-leucine sequency are, e.g., L-leucyl-L-alanyl-L-leucine, L-leucyl-L-alanyl-L-leucyl-L-alanine, L-alanyl-L-leucyl-L-analyl-L-leucine, or the like.

The oligopeptide-halogenated acetyl hydrazide derivative of a folic acid-antagonistic folic acid analogue of formula (III) and (IV), which is used in the present invention, is prepared by converting an oligopeptide ester derivative of a folic acid-antagonistic folic acid analogue of the following formula:

R'—CO—NH—Y—CO—OCH3 where R' and Y are the same as in the general formula (IV), to the hydrazide derivative by treatment with hydrazine hydrate and allowing the hydrazide to react with an activated ester of a halogenoacetic acid.

In the process according to the present invention, the oligopeptide-halogenated acetyl hydrazide derivative of folic acid-antagonistic folic acid analogue of formulas (III) and (IV) is preferably used in an amount of 1 -100 moles per mole of the antibody or its fragment. The reaction is carried out, for example, by adding the oligopeptide-halogenated acetyl hydrazide derivative of folic acid-antagonistic folic acid analogue dissolved in a small amount of a solvent, e.g., N,N-dimethyl-formamide, to a solution of the antibody or its fragment in a buffer solution of pH 6 -9 (preferably the protein concentration is adjusted to 1 -40 mg/ml), under stirring at 0 to 37° C. and keeping them for 15 minutes to 24 hours. Then, the reaction mixture is subjected to gel filtration or dialysis to remove the unreacting oligopeptide-halogenized acetyl hydrazide derivative of a folic acid-antagonistic folic acid analogue whereby the objective cytotoxic antibody conjugate of formula (I) is purified.

The present invention will be illustrated in detail in the following examples.

EXAMPLE 1

(a) Preparation of cytotoxic antibody conjugates

A mouse IgG2a monoclonal antibody (9.1 mg) to a mouse mammary tumor cells, MM46 was dissolved in 0.1 M Tris buffer solution (pH 8.0) containing 0.1 M sodium chloride and the solution was combined with 50 μl of an N,N-dimethylformamide solution (48.8 mg/ml) of a mixture of a methotrexate (abbreviated to MTX hereinafter) derivative of formula (III-1), where A represents L-leucyl-L-alanyl-L-Leucyl-L-alanyl and an MTX derivative of formula (III-2)

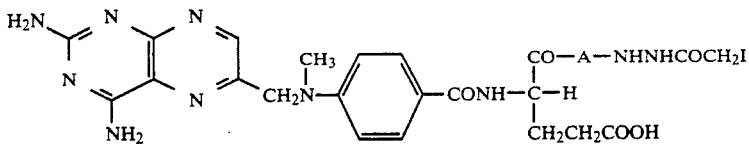

where A is defined as in formula (III-1), to effect the reaction at room temperature for 17 hours. After the reaction, the reaction mixture was thoroughly dialyzed against phosphate buffered saline (abbreviated to PBS) to give 6.8 mg of cytotoxic antibody conjugate in which on the average, 9.4 molecules of the MTX derivative are linked to 1 molecule of anti-MM46 antibody conjugate. The number of MTX molecules bound to IgG was determined by measurement of the absorbance at 280 nm and 372 nm (called A280 and A372, respectively). In other words, the concentration of MTX was calculated from A372, and that of IgG was obtained from A280 which had been corrected for the contribution from MTX. The average number of MTX molecules bound to an IgG molecule was calculated from the MTX and IgG concentrations thus determined.

The MTX derivative was obtained by condensation reaction of MTX with a peptide, L-leucyl-L-alanyl-L-leucyl-L-alanine methyl ester, in the presence of a condensation agent such as N,N'- dicyclohexylcarbodiimide, conversion of the methyl ester product into the hydrazide with hydrazine hydrate followed by iodoacetylation of the hydrazine residue with p-nitrophenyl iodoacetate.

(b) The cytotoxicity of the cytotoxic antibody conjugate against cultured tumor cells MM46 cells were suspended in RPMI 1640 media containing 10% of fetal calf serum and plated in a 96-well flat-bottomed microtest plate 0.2 ml every well. Then, 0.02 ml of the cytotoxic antibody conjugate (prepared in (a)) solutions of various concentrations in the media were admixed and the cells were cultured in a 5% carbon dioxide atmosphere at 37° C. for 3 days. These procedures were operated under germ-free conditions. After the cell culture, 0.02 ml of 3% trypan blue solution was added to the culture mixture to count the viable cells unstained with the dye under a microscope.

The results were summarized in Table 1. MM46 cells proliferated, in case of no addition, to about 1 ×106 cells/ml after culture for 3 days, but the viable cells decreased with the amounts added of the cytotoxic antibody conjugate which was prepared in (a).

Especially, the concentration of 10 μM by MTX equivalence exerted high cytotoxic effect and the viable cells were found only 1% or less compared with that in the culture without addition of the antibody conjugate.

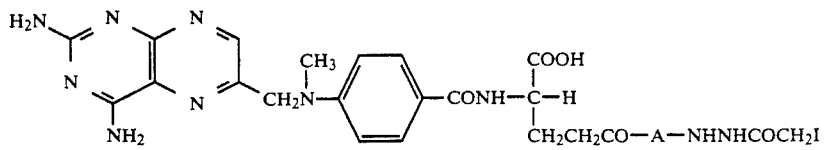

TABLE 1

| Concentration of the conjugate (μM by MTX equivalence) | Counts of viable cells after 3-day culture × 10⁴ cells/ml | inhibition rates of viable cells (%) |
| --- | --- | --- |
| 0 | 102.9 | — |
| 0.01 | 87.4 | 15 |
| 0.1 | 23.4 | 77 |
| 1 | 2.9 | 97 |
| 10 | 1.0 | 99 |

(c) The evidence of the reaction between iodoacetyl hydrazide derivative of methotrexate and the amino group of the antibody molecule (immuno-globulin)

A hundred μl of iodoacetyl hydrazide derivative of methotrexate of formula (III-1) (MTX derivative) solution in N,N-dimethylformamide (13.4 mg/ml) were added to 1 ml of a rabbit Y-globulin (abbreviated to RGG) solution (5 mg/ml, dissolved in 0.1 M Tris buffer solution (pH 8.0) containing 0.1 M sodium chloride). At this step, in one experiment, 1 M ethanolamibe was previously added to the RGG solution, while in the other, 0.9% sodium chloride solution, in amounts of 100 μl, respectively.

After 14 hour reaction at room temperature, the reaction mixture was thoroughly dialyzed against 10 M phosphate buffer solution containing 0.14 M sodium chloride (pH 7.2) (abbreviated to PBS) to remove reagents of low molecular weights or the like. The dialysate was centrifuged and the supernatant was measured on A280 and A372. The concentration of MTX was calculated from A372, and that of IgG was obtained, from A280 which had been corrected for the contribution from MTX. Thus, the reaction rate of the MTX derivative and the binding ratio of MTX to RGG were calculated.

The results are shown in Table 2.

TABLE 2

| No. | Ethanolamine | MTX derivative reaction rate (%) | Binding ratio of MTX to RGG (mole/mole) |
| --- | --- | --- | --- |
| 1 | added | 1.5 | 0.6 |
| 2 | not added | 14.5 | 5.8 |

Under above-cited conditions, 5.8 molecules of the MTX derivative were found to combine with 1 molecule of RGG on the average, in case of no addition of ethanolamine. When ethanolamine was added, the reaction was markedly inhibited and only 0.6 molecules of the MTX derivative linked per molecule of RGG. These facts evidently show that the reaction between the MTX derivative and RGG proceeds through amino groups.

EXAMPLE 2

The comparison on cytotoxicity between anti-MM46 cytotoxic antibody conjugate, nonspecific globulin conjugate and MTX derivative before globulin conjugation Instead of anti-MM46 antibody, a normal (or nonspecific) mouse-Y-globulin was used to prepare a nonspecific globulin conjugate in which 7.9 molecules of the MTX derivative in Example 1 were bound to 1 molecule of globulin on the average in the same manner as in Example 1.

As in Example 1 (b), the cytotoxicity against MM46 cultured cells was examined for anti-MM46 cytotoxic antibody conjugate prepared in Example 1 (a), the nonspecific globulin conjugate and the MTX derivative before conjugation with globulin.

The results were summarized in Table 3. The anti-MM46 cytotoxic antibody conjugate revealed cytotoxic effect at much lower concentrations than the two other substances. In other words, the concentration of the antibody conjugate necessary for suppressing the count of MM46 viable cells to 50% of the count in case of no addition of the antibody conjugate was only 1/14 of that of the nonspecific conjugate.

Further, the difference in activity between the anti-MM46 conjugate bearing MTX through the tetrapeptide according to the present invention and the corresponding nonspecific conjugate was compared with the difference between a conventional anti-MM46 conjugate in which MTX was directly bound to the antibody prepared by using an activated ester of MTX and the corresponding nonspecific conjugate and the former was found to be 54 times greater than the latter.

TABLE 3

| Drug concentration (by MTX equivalence, μM) | Viable cell number after 3-days culture (× 10⁴ cells/ml) | | |
| --- | --- | --- | --- |
| | Antibody conjugate | Nonspecific globulin conjugate | MTX deriv. |
| 0 | | 62 | |
| 0.010 | 59 | — | — |
| 0.032 | 40 | — | — |
| 0.10 | 15 | — | — |
| 0.32 | 6.0 | 54 | 66 |
| 1.0 | — | 10 | 20 |
| 3.2 | — | 1.6 | 4.2 |

EXAMPLE 3

Preparation of anti-human melanomacytotoxic antibody conjugate and the evaluation on its antitumor activity Instead of anti-MM46 antibody, a mouse IgG2a monoclonal antibody to human melanoma cells and normal (nonspecific) rabbit-Y-globulin were employed to prepare, by the same procedures as in Example 1 (a), anti-human melanoma cytotoxic antibody conjugate and a nonspecific globulin conjugate. These conjugates were subjected to the following antitumor evaluation tests.

Three groups of 5 nude mice, to which human melanoma cells, KHm-1, were implanted subcutaneously on the flank, were given anti-human melanoma cytotoxic antibody conjugate, nonspecific globulin conjugate and a mixture of anti-human melanoma antibody and MTX in the same amount as in the anti-human melanoma cytotoxic antibody conjugate, respectively, 3 times in 5-day intervals starting 10 days after tumor implantation.

Nude mice (10 mice) to which the drugs were not given were provided as a control. The tumors were excised 30 days after tumor implantation and weighed. Marked suppression of tumor growth was observed only in the group treated with antihuman melanoma cytotoxic antibody conjugate. The average weight of the tumors in this group was 27% of that in the control group.

EXAMPLE 4

Instead of a mixture of MTX derivatives of formula (III-1) and formula (III-2) in Example 1, a mixture of aminopterin (abbreviated to AMN hereinafter) derivatives of formula (III-3)

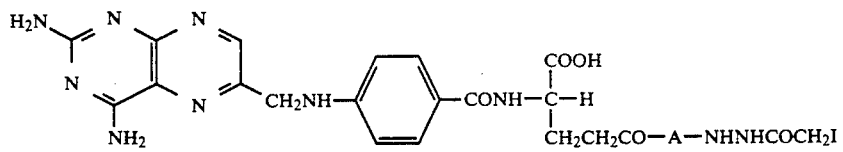

where A is defined as in formula (III-1), and formula (III-4)

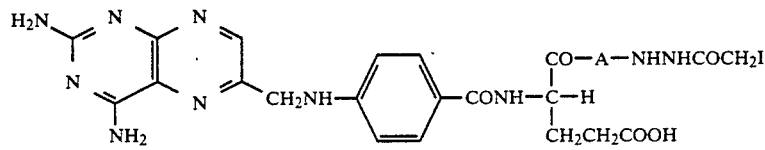

where A is defined as in formula (III-1) was employed to prepare anti-MM46 cytotoxic antibody conjugate in which 7.2 molecules of the aminopterin derivatives were bound to 1 molecule of IgG on the average in the same manner as in Example 1 (a).

EXAMPLE 5

Instead of a mixture of MTX derivatives of formula (III-1) and formula (III-2) in Example 1, a mixture of MTX derivatives of formula (III-5)

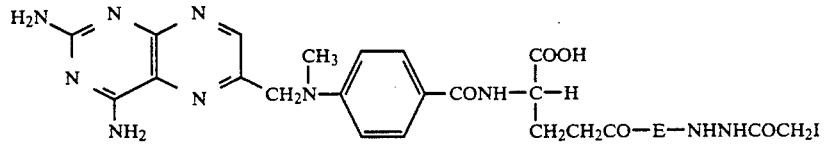

where E represents L-leucyl-L-alanyl-L-leucyl group, and formula (III-6)

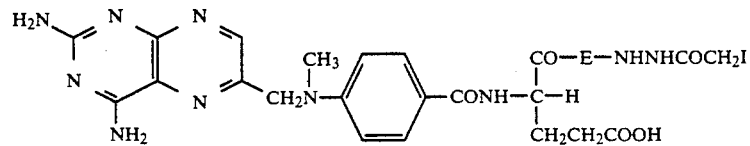

where E is defined as in formula (III-5) was used to prepare anti-MM46 cytotoxic antibody conjugate in which 5.7 molecules of the MTX derivatives were bound to 1 molecule of IgG on the average.

EXAMPLE 6

Anti-human melanoma antibody, instead of anti-MM46 antibody in Example 1, and a mixture of AMN derivatives of formula (III-7)

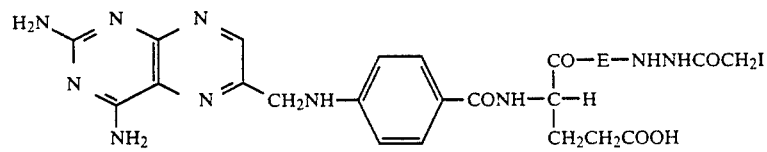

where E is defined as in formula (III-5), and formula (III-8)

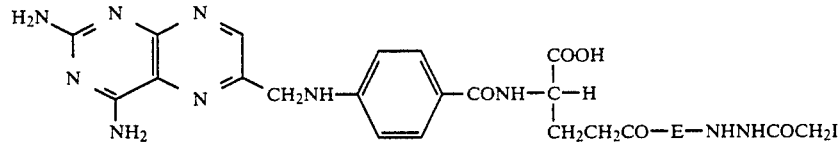

where E is defined as in formula (III-5), instead of the mixture of the MTX derivatives of formula (III-1) and formula (III-2), were employed to prepare anti-human melanomacytotoxic antibody conjugate in which 6.1 molecules of the AMN derivatives were bound to 1 molecule of IgG on the average in the same manner as in Example 1-(a).

EXAMPLE 7

Instead of a mixture of MTX derivatives of formula (III-1) and formula (III-2) in Example 1, a mixture of MTX derivatives of formula (III-9)

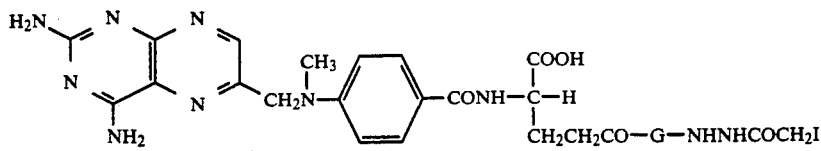

where G represents L-alanyl-L-leucyl-L-alanyl-L-leucyl group, and formula (III-10)

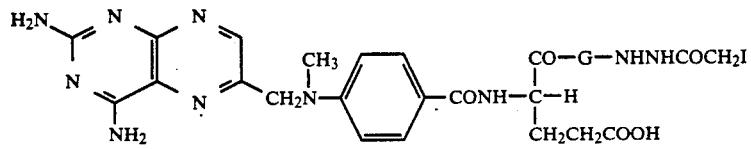

where G is defined as in formula (III-9) was used to prepare anti-MM46 cytotoxic antibody conjugate in which 8.2 molecules of the MTX derivatives bound to 1 molecule of IgG on the average in the same manner as in Example 1 (a).

EXAMPLE 8

Instead of a mixture of MTX derivatives of formula III-1) and formula (III-2) in Example 1, a mixture of 10-ethyl-10-deaza-aminopterin derivatives of formula (III-11)

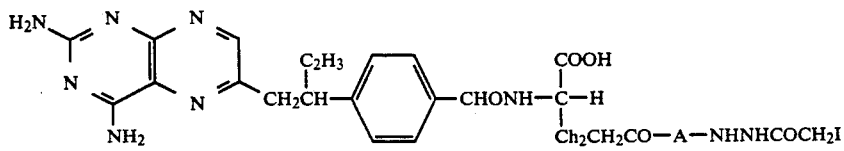

where A is defined as in formula (III-1), and formula (III-12)

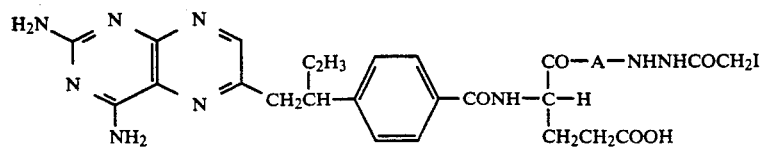

where A is defined as in formula (III-1) was used to prepare anti-human melanoma cytotoxic antibody conjugate in which 8.1 molecules of the 10-ethyl-10-deaza-aminopterin derivatives were bound to 1 molecule of IgG on the average in the same manner as in Example 1 (a).

EXAMPLE 9

Instead of a mixture of MTX derivatives of formula (III-1) and formula (III-2) in Example 1, a mixture of AMN derivatives of formula (III-13)

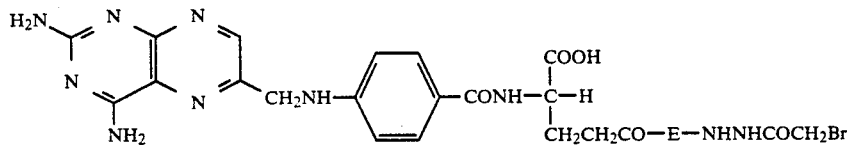

where E is defined as in formula (III-5), and formula (III-14)

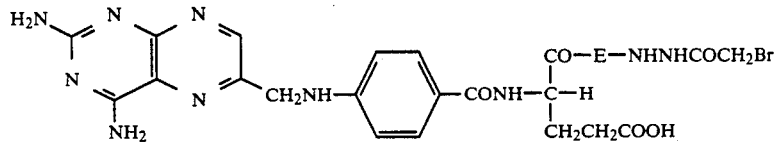

where E is defined as in formula (III-5) was used to prepare anti-MM46 cytotoxic antibody conjugate in which 2.2 molecules of the AMN derivatives were bound to 1 molecule of IgG on the average in the same manner as in Example 1 (a).

We claim:

1. Cytotoxic antibody conjugates wherein an antibody or its fragment which binds to antigenic cells is bound to a folic acid-antagonistic folic acid analgogue through an oligopeptide, wherein said cytotoxic antibody conjugate is represented by general formula (I)

(R'—CO—NH—Y—CO—NHNHCOCH2—NH)
   Ab .....(I)

where R' represents, together with CO, the residual group of a folic acid-antagonistic folic acid analogue, —NH—Y—CO—represents the residual group of an oligopeptide containing L-leucyl-L-alanyl-L-leucine, Ab represents an antibody or its fragment which binds to antigenic cells, and the N-atom adjacent to Ab is the nitrogen atom originating from the antibody or its fragment, and n is an integer of from 1 to 30.

2. Cytotoxic antibody conjugates according to claim 1 wherein the antibody is a monoclonal antibody.

3. Cytotoxic antibody conjugates according to claim 1 wherein the oligopeptide is L-leucyl-L-alanyl-L-leucyl-L-alanine, L-alanyl-L-leucyl-L-alanyl-L-leucine, or L-leucyl-L-alanyl-L-leucine.

4. Cytotoxic antibody conjugates according to claim 1 wherein the folic acid-antagonistic folic acid analogue is methotrexate, aminopterin or 10-ethyl-1-0deaza-aminopterin.

5. A process for preparation of cytotoxic antibody conjugates of general formula (II)

(RCONHNHCOCH2NH Ab ..... (II)

where R represents, together with CO, a monovalent organic group originating from a cytotoxic substance, Ab represents antibody or its fragment which binds to antagenic cells, the N-atom binding with Ab orginates from an antibody or its fragment, and n is an integer of from 1 to 30, characterized by reaction of an antibody or its fragment which binds to antigenic cells with a halogenated acetyl hydrazide derivative of a cytotoxic substance having a general formual (III)

RCONHNHCOCH2X ..... (III)

wherein the definition of R is the same as in formual (II), and X represents a halogen.

6. A process for preparation of cytotoxic antibody conjugates according to claim 5 wherein RCO in formulas (II) and (III) is represented by the formual (IV)

R'—CO—NH—Y—CO—..... (IV)

wherein R' represents, together with the adjacent CO, and residual group of a folic acid-antagonistic folic acid analogue, and —NH—Y—CO—represents the residual group of an oligopeptide.

7. A process for preparation of cytotoxic antibody conjugates according to claim 6 wherein —NH—Y—CO—in general formula (IV) is a residual group of oligopeptide containing L-leucyl-L-alanyl-L-leucine.

* * * * *